United States Patent [19]

Papenfuhs

[11] Patent Number: 4,922,014
[45] Date of Patent: May 1, 1990

[54] PROCESS FOR THE PREPARATION OF OXETHYLMERCAPTOBENZALDEHYDES AND THEIR OXIDATION PRODUCTS

[75] Inventor: Theodor Papenfuhs, Frankfurt am Main, Fed. Rep. of Germany

[73] Assignee: Hoechst Aktiengesellschaft, Frankfurt am Main, Fed. Rep. of Germany

[21] Appl. No.: 246,802

[22] Filed: Sep. 20, 1988

[30] Foreign Application Priority Data

Sep. 22, 1987 [DE] Fed. Rep. of Germany ....... 3731763

[51] Int. Cl.$^5$ .......................................... C07C 51/285
[52] U.S. Cl. .................................... 562/418; 568/31; 568/41
[58] Field of Search ............................ 562/418, 31, 41

[56] References Cited

U.S. PATENT DOCUMENTS

| | | | |
|---|---|---|---|
| 2,763,692 | 9/1956 | Gregory | 568/31 |
| 2,802,033 | 8/1957 | Gregory | 568/31 |
| 3,098,096 | 7/1963 | Feeman | 260/544 |
| 3,787,443 | 1/1974 | Erickson | 568/31 |
| 3,956,395 | 5/1976 | Meyer | 260/607 |

FOREIGN PATENT DOCUMENTS

| | | |
|---|---|---|
| 0089154 | 9/1983 | European Pat. Off. |
| 2401665 | 7/1974 | Fed. Rep. of Germany |
| 1416116 | 12/1975 | United Kingdom |

OTHER PUBLICATIONS

R. Schwyzer et al., Helv. Chim. Acta 67, 1316-1327 (1984).
J. Schwartz, Synth. Commun. 16, 565-570 (1986).

Primary Examiner—Michael L. Shippen

[57] ABSTRACT

Process for the preparation of oxethylmercaptobenzaldehydes and their oxidation products of the formula (I)

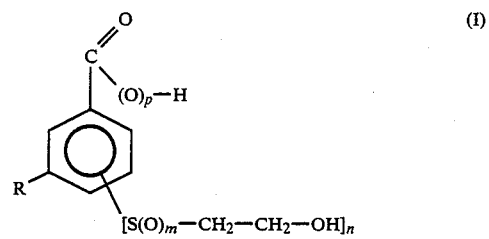

in which R denotes a hydrogen, fluorine, chlorine, bromine or iodine atom, m denotes the number 0 or 2, n denotes the number 1 or 2, and p denotes the number 0 or 1, with the proviso that p is 0 if m is 0, and the side-chain $-S(O)_m-CH_2-CH_2-OH$ is in the ortho and/or para position to the aldehyde or carboxyl group, can be prepared by condensing 1 mole of a halobenzaldehyde of the general formula (II)

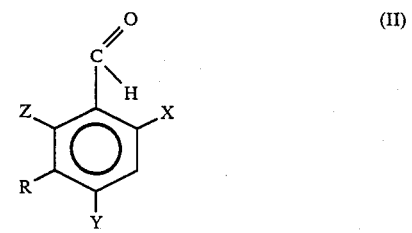

in which R, X, Y and Z represent hydrogen, fluorine, chlorine, bromine or iodine atoms, with the proviso that R, X, Y and Z can be in total 1, 2 or 3 halogen atoms, where R is a halogen atom if R, X, Y and Z together represent 3 halogen atoms, in aqueous medium with about 1.0 to 1.5 moles of mercaptoethanol (per halogen atom to be exchanged) in the presence of the acid-binding agents at or about 70° C. about 150° C., to give the oxethylmercaptobenzaldehydes and oxidizing these to give the oxethylsulfonylbenzoic acids using at least the amount of hydrogen peroxide necessary in each case at about 40° C. to about 110° C. in the presence of a tungsten(VI) compound as a catalyst.

12 Claims, No Drawings

PROCESS FOR THE PREPARATION OF OXETHYLMERCAPTOBENZALDEHYDES AND THEIR OXIDATION PRODUCTS

The present invention relates to an economically and ecologically advantageous process for the preparation of oxethylmercaptobenzaldehydes and their oxidation products (oxethylsulfonylbenzaldehydes and oxethylsulfonylbenzoic acids) in high yields and good quality.

The said compounds are commercially important precursors. Thus, 4-oxethylsulfonylbenzoic acid is used, for example, as a solid phase link for the synthesis of specific oligonucleotides (Tetrahedron Lett. 25, 3967-70 (1984); Helv. Chim. Acta 1984, 1316-27). Oxethylsulfonylbenzoic acids are in addition important precursors for the preparation of azo dyes which react with fibers (U.S. Pat. No. 3,098,096). 2- and 4-oxethylmercaptobenzaldehydes and their oxidation products are valuable intermediates for the preparation of optical brighteners of the 1,4-distyrylbenzene series (DE-OS No. 2,401,665) and for the preparation of pharmaceuticals (EP-OS No. 0,089,154).

Specific processes are already known for the preparation of the said compounds:

2- and 4-oxethylmercaptobenzaldehyde are obtained by reaction of 2- or 4-chlorobenzaldehyde with mercaptoethanol/KOH or sodium methylate. Dimethyl sulfoxide/carbon tetrachloride is used as a solvent (DE-OS No. 2,401,665, pages 37-40, Table IV). In EP-OS No. 0,089,154, the corresponding reaction of 4-fluorobenzaldehyde with mercaptoethanol is described (pages 59/47). In a general method for the preparation of alkylmercaptobenzaldehydes from bromobenzaldehydes and alkylmercaptans, dimethylformamide is used as a solvent and sodium hydride (dispersed in mineral oil) as a base (Synth. Commun. 16, 565-70 (1986)). Oxethylsulfonylbenzaldehydes are mentioned in DE-OS No. 2,401,665 as intermediates, but, however, no details are given there on their synthesis. 4-Oxyethylsulfonylbenzoic acids have hitherto been exclusively prepared from precursors which already contain the carboxyl group. Thus 4-oxethylmercaptobenzoic acid ("CAMET") results by reaction of 4-mercaptobenzoic acid with chloroethanol (U.S. Pat. No. 3,098,096) or ethylene oxide (Helv. Chim. Acta 1984, 1316-27). Its oxidation to 4-oxethylsulfonylbenzoic acid ("CASET (2)") is described using H$_2$O$_2$ with heavy metal catalysis (Helv. Chim. Acta 1984, 1316-27) or using hypochlorite (U.S. Pat. No. 3,098,096). The lastmentioned compound can also be prepared in the classical manner from 4-chlorosulfonylbenzoic acid (reduction to sulfinic acid and its reaction with ethylene oxide or chloroethanol) (U.S. Pat. No. 3,098,096).

The known processes previously mentioned are without exception only suitable for the preparation of specific intermediates of the general formula (I) indicated further below and moreover have the following serious disadvantages:

In the exchange reactions of the halobenzaldehydes, expensive dipolar-aprotic solvents (dimethylformamide or dimethyl sulfoxide) and mostly, in addition, bases which are difficult to handle (alkali metal alcoholates or hydrides) are used. In addition, only moderate yields and purities are obtained in this process so that, as a rule, a purification step (distillation, extraction by means of chloroaliphatics or recrystallization from aromatics, for example benzene) must be carried out subsequently. Solvent cycles are indispensable.

The oxethylation reactions for the formation of the oxethylmercapto- or oxethylsulfonylbenzoic acids require only poorly and therefore uneconomically available starting compounds (mercaptobenzoic acids, 4-chlorosulfonylbenzoic acid). On account of the by-products inevitably produced (salts, chloroethanol, low valency sulfur compounds), complicated purification processes for product and mother liquor have to be added to these oxethylation reactions for ecological reasons.

Some of the oxidation reactions for the preparation of the oxethylsulfonylbenzoic acids require partially ecologically unfavorable reagents (such as sodium hypochlorite) and have hitherto not been described for the reaction of corresponding benzaldehydes.

Surprisingly, it has now been found that oxethylmercaptobenzaldehydes and their oxidation products oxethylsulfonylbenzaldehydes and oxethylsulfonylbenzoic acids of the general formula (I)

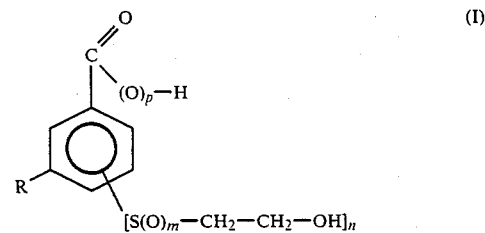

in which R denotes a hydrogen, fluorine, chlorine, bromine or iodine atom, m denotes the number 0 or 2, n denotes the number 1 or 2, and p denotes the number 0 or 1, with the proviso that p is 0 if m is 0, and the sidechain —S(O)$_m$—CH$_2$—CH$_2$—OH is in the ortho and/or para position to the aldehyde or carboxyl group, can be prepared in an economically and ecologically advantageous manner in high yields and good quality by condensing 1 mole of a halobenzaldehyde of the general formula (II)

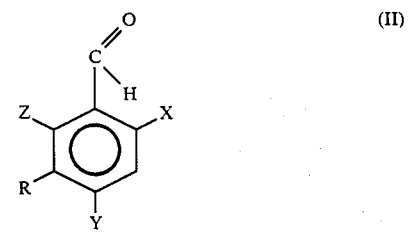

in which R, X, Y and Z represent hydrogen, fluorine, chlorine, bromine or iodine atoms, with the proviso that R, X, Y and Z can be in total 1, 2 or 3 halogen atoms, where R is a halogen atom if R, X, Y and Z together represent 3 halogen atoms, in aqueous medium (in the absence of organic solvents) with about 1.0 to 1.5 moles, preferably about 1.25 to 1.4 moles, of mercaptoethanol (per halogen atom to be exchanged) in the presence of acid-binding agents at temperatures of about 70° C. to about 150° C., preferably about 90° C. to about 120° C., to give the corresponding oxethylmercaptobenzaldehydes and oxidizing these (optionally mixed with low amounts of the corresponding Cannizzaro products oxethylmercaptobenzyl alcohol and oxethylmercaptobenzoic acid), optionally after the necessary intermediate isolation, to give the corresponding oxethylsulfonylbenzaldehydes or oxethylsulfonylbenzoic acids using at least the amount of hydrogen peroxide necessary in each case at temperatures of about 40° C. to about 110° C., preferably about 60° C. to about 95° C., at (to obtain the corresponding oxethylsulfonylbenzaldehyde) pH<5, preferably pH 1–4, or at (to obtain the corresponding oxethylsulfonylbenzoic acids) pH>8, preferably 9–13, in each case in the presence of a tungsten-(VI) compound as a catalyst.

Starting compounds which may be mentioned, for example, are 2-chlorobenzaldehyde, 4-chlorobenzaldehyde, 2,4-dichlorobenzaldehyde, 2,5-dichlorobenzaldehyde, 2,6-dichlorobenzaldehyde, 3,4-dichlorobenzaldehyde, 2,3-dichlorobenzaldehyde and 2,4,5-trichlorobenzaldehyde and also the corresponding fluorine or bromine derivatives.

Suitable acid-binding agents are hydroxides, oxides and carbonates of alkali metals and alkaline earth metals, the alkali metal hydroxides and alkaline earth metal hydroxides being preferred. Acid-binding agents which may be mentioned individually are caustic potash or potassium hydroxide solution, caustic soda or sodium hydroxide solution and magnesium oxide.

In detail, the condensation is carried out by adding 1.0 to 1.5 times the molar amount, preferably 1.25 to 1.4 times the molar amount of mercaptoethanol (per halogen atom to be exchanged) and the amount equivalent to this amount of the acid-binder successively to an aqueous emulsion or suspension of the halobenzaldehyde, stirring the mixture for 6 to 20 hours, preferably 8 to 15 hours, at 70° to 150° C., preferably 90° to 120° C., optionally removing unreacted halobenzaldehyde from the reaction mixture by distillation using steam and isolating the oxethylmercaptobenzaldehyde formed of the formula (I) mentioned by filtration or phase separation, if appropriate after previously cooling to temperatures of 0° to 50° C., preferably 10° to 25° C.

Depending on the reaction temperature, operation under atmospheric pressure or in a closed system is appropriate.

The oxidation of the oxethylmercaptobenzaldehydes thus obtainable leads, in a pH-dependent manner, to defined oxidation products of the said general formula (I): the corresponding oxethylsulfonylbenzaldehydes are thus obtained at pH values under 5, preferably at pH 1 to 4, using 2 moles of $H_2O_2$ per oxethylmercapto group, provided the oxidation is catalyzed in a manner known per se using tungsten(VI) compounds (for example $Na_2WO_4$, $WO_3$).

On the other hand, at pH values above 8 (preferably 9 to 13) the aldehyde function also is oxidized to the carboxyl function so that, in a sequence not to be specified more closely, the corresponding oxethylsulfonylbenzoic acid results as the final product (the intermediate compounds oxethylmercapto and oxethylsulfinylbenzoic acid cannot be expressed in a defined form). For the complete conversion of the mono-oxethylmercaptobenzaldehyde into the mono-oxethylsulfonylbenzoic acid, at least 3 moles of hydrogen peroxide are necessary; if the starting compound contains 2 oxethylmercapto groups, the $H_2O_2$ requirement is increased to at least 5 moles. In practice, an $H_2O_2$ excess of 10 to 60 %, preferably 20 to 35 %, is advantageously used in order to lead the oxidation to completion in justifiable reaction times and to account for the unavoidable partial self-decomposition of the hydrogen peroxide.

In detail, the oxidation is carried out by emulsifying the corresponding oxethylmercaptobenzaldehyde suspended in water, optionally in the presence of an emulsifier, setting the desired pH value (pH 1 to 4 for the sole oxidation of the oxethylmercapto group, pH 9 to 13 for the preparation of the oxethylsulfonylbenzoic acid) using mineral acid or alkali metal liquor, adding a compound of 6-valent tungsten (sodium tungstate or $WO_3$) in low amounts (0.1 to 10 g, preferably 1 to 5 g per mole of mercapto compound) as an oxidation catalyst, adding the necessary amount of aqueous, preferably 25 to 40 % strength, hydrogen peroxide dropwise within 15 to 120 minutes after heating to 40° C. to 110° C., preferably 60° C. to 95° C., and stirring at reaction temperature until completion of the reaction (testing by, for example, high-performance liquid chromatography ("HPLC") or thin-layer chromatogram ("DC"). The target compound formed can then be isolated, if appropriate after cooling to temperatures of 0° C. to 50° C., preferably 10° C. to 25° C., by filtration or extraction.

In many cases a one-pot process has proved particularly advantageous, in which the oxethylmercaptobenzaldehyde formed in the first step is not isolated, but directly oxidized in the reaction mixture by means of hydrogen peroxide in a manner according to the invention to give the desired target compound, after setting the necessary pH value and adding a tungsten(VI) catalyst.

The examples below illustrate the invention in greater detail without limiting it thereto.

The parts by weight given bear the same relationship to the parts by volume mentioned as g to ml (or kg to l).

EXAMPLE 1

114.8 parts of molten 4-chlorobenzaldehyde are added dropwise at 40° C. within 15 minutes with good stirring to a mixture of 150 parts of water, 63.4 parts of caustic potash (85% pure) and 88.3 parts of mercaptoethanol, and the mixture is subsequently heated to 90° to 92° C. and stirred for about 18 hours at this temperature. The progress of the reaction is followed by thin-layer chromatography. When starting material is no longer detectable, 320 parts of water are added to dissolve the deposited inorganic salts, the mixture is cooled with stirring to 10° to 20° C. and the 4-oxethylmercaptobenzaldehyde which crystallizes during cooling in granules is filtered off with suction. After washing with 200 parts of ice-water and drying in vacuo at 40° C., 137.6 parts of 4-oxethylmercaptobenzaldehyde of melting point 58° to 60° C. and a purity of 96.9% (HPLC) are obtained. The product contains about 2% of 4-oxethylmercaptobenzyl alcohol (from the Cannizzaro reaction occurring in parallel) which can be removed by stirring once with 300 parts of icewater with a moderate loss of yield owing to its water solubility. 126 parts of 4-oxethylmercaptobenzaldehyde of melting point 60° to 61° C. and a purity of >99% are obtained.

4.5 parts of 4-oxethylmercaptobenzoic acid of melting point 149° to 152° C. (formed as the corresponding Cannizzaro product) can be isolated from the mother liquor of the reaction by acidifying, filtering off and drying.

If an equivalent amount of magnesium oxide is used instead of the caustic potash and the reaction is otherwise carried out in the manner indicated, then the 4-oxethylmercaptobenzaldehyde is obtained in comparable yield and quality.

EXAMPLE 2

140 parts of 85% strength caustic potash are added in 5 portions within 30 minutes, at 50° to 55° C., to a stirred mixture of 250 parts of water, 195 parts of mercaptoethanol and 229.6 parts of 2-chlorobenzaldehyde. The mixture is subsequently heated to 105° to 110° C. (reflux) and stirred for about 15 hours at this temperature. Following the reaction by thin-layer chromatography shows that after this time only small amounts of 2-chlorobenzaldehyde are still present in the reaction mixture. These are removed by indirect steam distillation (distilling over the vapor until the distillate is monophasic). In this case, 6.5 parts (2.8% of theory) of 2-chlorobenzaldehyde are recovered (phase separation of the distillate) which can be employed again in the next batch.

550 parts of water are subsequently added to the hot reaction mixture to dissolve the inorganic salts and it is stirred until it has cooled to 20° to 25° C. After turning off the stirrer, the reaction mixture separates into 2 phases. The organic phase is separated off, stirred twice with deionized water (250 to 300 parts) and water is removed by brief incipient distillation in vacuo (100 to 150 mbar). 280.0 parts of 2-oxethylmercaptobenzaldehyde of purity 98.4% (HPLC) are obtained.

(Analysis: S: 17.5/17.7%; calc.: 17.58%/residual chlorine: <0.3%; calc. 0.0%). If the caustic potash is replaced by an aliquot amount of 50% strength sodium hydroxide solution which is added dropwise at a constant rate in the indicated time, and the reaction is otherwise carried out in a corresponding manner, then 10.4 parts of unreacted 2-chlorobenzaldehyde are obtained as a distillate and 273.8 parts of 2-oxethylmercaptobenzaldehyde of comparable quality are obtained.

EXAMPLE 3

A mixture of 200 parts of water, 90.0 parts of mercaptoethanol and 143.0 parts of 3,4-dichlorobenzaldehyde is warmed to 60° to 65° C. 110.0 parts of 50% strength potassium hydroxide solution are added dropwise at a constant rate at this temperature with good stirring within 20 minutes and the mixture is subsequently heated to 85° to 90° C. The reaction is completed by stirring for about 12 hours at this temperature (checking by means of HPLC for the absence of 3,4-dichlorobenzaldehyde).

180 parts of water are added to the hot reaction mixture to dissolve the inorganic salts, the mixture is subsequently cooled to 15° to 20° C. with vigorous stirring, and the deposited 3-chloro-4-oxethylmercaptobenzaldehyde is filtered off with suction, washed neutral with water and dried in vacuo at 40° to 50° C. to constant weight.

165.4 parts of 3-chloro-4-oxethylmercaptobenzaldehyde of melting point 77° to 79° C. and a purity of 97.3% (HPLC) are obtained. The product contains about 1% of 3-chloro-4-oxethylmercaptobenzyl alcohol. These impurities can be removed by stirring with 300 parts of warm water at 60° C. In this case, 161.9 parts of 3-chloro-4-oxethylmercaptobenzaldehyde of melting point 79° to 80° C. result (purity by HPLC: 98.9%). If the amount of mercaptoethanol and potassium hydroxide solution is increased by about 10% in the reaction described previously, the reaction time is shortened by about 2 hours. Yield and quality remain unchanged.

EXAMPLE 4

390 parts of mercaptoethanol are added dropwise within 60 minutes with stirring at 15° to 20° C. to 1,190 parts of 20% strength potassium hydroxide solution, the mixture is heated to 70° to 75° C. and 286 parts of a 2,4-dichlorobenzaldehyde melt heated to 75° to 80° C. are then added all at once.

The mixture is swiftly heated further to 90° to 95° C., kept at this temperature for 6 hours and the temperature is then raised to 110° to 115° C. (reflux). The mixture is stirred at reflux until starting material is no longer detectable by HPLC and a nearly homogeneous reaction product (>95 area per cent) is identifiable, which requires about 13 to 15 hours. 500 parts of water are subsequently added to dissolve the inorganic salts, the mixture is cooled with stirring to 0° to 5° C. and the deposited precipitate is isolated by filtration.

After washing with 500 parts of ice-water and drying in vacuo at room temperature, 335.2 parts of 2,4-bis-oxethylmercaptobenzaldehyde of melting point 76° to 78° C. and a purity of 98.1% (HPLC) are obtained. (Analysis: S: 25.0/24.8%; calc. 24.81%/residual chlorine: <0.3%; calc. 0.0%).

EXAMPLES 5 to 8

If, in Examples 1 to 4, the aldehyde employed is replaced by aliquot parts of the aldehydes shown in Table 1 and the reaction is otherwise carried out in the manner indicated, until detection of completion of the reaction can be produced by chromatography, then the oxethylmercaptobenzaldehydes of the general formula II (see below) evident from Table 1 below are obtained with the purities (HPLC) shown in the yields stated there.

TABLE 1

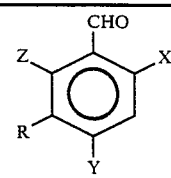
(II)

| Ex. | Starting compound | Product X | Y | Z | R | Yield | RG |
|---|---|---|---|---|---|---|---|
| 5 | 2,5-Dibromo-benzaldehyde | SC₂H₄OH | H | H | Br | 94.4% | 97.8% |
| 6 | 2,6-Dichloro-benzaldehyde | SC₂H₄OH | H | SC₂H₄OH | H | 81.0% | 98.4% |
| 7 | 2,3-Dichloro-benzaldehyde | H | H | SC₂H₄OH | Cl | 75.8% | 97.1% |

TABLE 1-continued

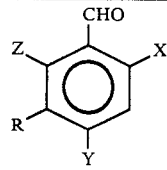

| Ex. | Starting compound | Product X | Y | Z | R | Yield | RG |
|---|---|---|---|---|---|---|---|
| 8 | 2,4,5-Trichloro-benzaldehyde | SC$_2$H$_4$OH | SC$_2$H$_4$OH | H | Cl | 91.2% | 97.5% |

("RG" means purity)

EXAMPLE 9

364 parts of 4-oxethylmercaptobenzaldehyde, 500 parts of water and 6 parts of sodium tungstate are stirred at 60° C. and the emulsion formed is adjusted to pH 1.5 using 2N sulfuric acid. 408 parts of 35% strength hydrogen peroxide are added dropwise during the course of 2 hours, the internal temperature is subsequently raised to 75° C. and the mixture is stirred for about 14 hours, until a thin-layer chromatographic analysis indicates the absence of 4-oxyethylmercaptobenzaldehyde. The mixture is then cooled with stirring to room temperature and adjusted to a pH of 8.5 using 2N sodium hydroxide solution, and the suspended 4-oxethylsulfonybenzaldehyde is filtered off with suction, washed neutral with cold water and dried in vacuo at 50° C.

340 parts of 4-oxethylsulfonylbenzaldehyde of melting point 111° to 113° C. and a purity (HPLC) of 97.2% are obtained. The compound shows all the typical aldehyde reactions.

EXAMPLE 10

If the 4-oxethylmercaptobenzaldehyde in Example 9 is replaced by 2-oxethylmercaptobenzaldehyde and the reaction is otherwise carried out in the manner indicated, then the 2-oxethylsulfonylbenzaldehyde is obtained in comparable yield and quality.

EXAMPLE 11

546 parts of 4-oxethylmercaptobenzaldehyde, 780 parts of water, 15 parts of Arkopal N100 (R) (commercial product of HOECHST AG) and 8 parts of sodium tungstate are stirred at 60° C. and the emulsion resulting in the course of this is adjusted to pH 9 using 4N sodium hydroxide solution. 1,000 parts of 35% strength hydrogen peroxide are now added dropwise in the course of 60 minutes, the temperature being allowed to increase to 95° C., and the mixture is heated for 15 to 20 hours at 95° C. until a HPLC sample indicates complete conversion. 500 parts of water are subsequently added, the mixture is cooled to room temperature with stirring and adjusted to pH 6 using 2N hydrochloric acid, and the precipitate formed is filtered off with suction.

After washing to neutral using ice-water and drying in vacuo at 80° C., 614 parts of 4-oxethylsulfonylbenzoic acid of melting point 169° to 172° C. and a purity of 95.8% (HPLC) are obtained. A sample recrystallized from water with the addition of activated charcoal shows a melting point of 190° C. and a purity of 99.1% (HPLC).

EXAMPLES 12 to 16

If the 4-oxethylmercaptobenzaldehyde shown in Example 11 is replaced by aliquot parts of the aldehydes indicated in Table 2 below and the reaction is otherwise carried out in an analogous manner, until evidence of complete reaction is produced chromatographically, then the oxethylsulfonylbenzoic acids evident from Table 2 of the general formula (III) shown below are obtained with the purities (HPLC) and yields indicated therein.

TABLE 2

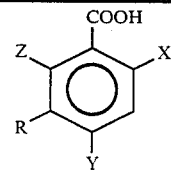

| Ex. | Starting compound | Product X | Y | Z | R | Yield | RG |
|---|---|---|---|---|---|---|---|
| 12 | 2-Oxethylmercapto benzaldehyde | SO$_2$C$_2$H$_4$OH | H | H | H | 85.9% | 96.5% |
| 13 | 3-Chloro-4-oxethyl-mercaptobenzaldehyde | H | SO$_2$C$_2$H$_4$OH | H | Cl | 92.3% | 98.1% |
| 14 | 2,4-Bisoxethyl-mercaptobenzaldehyde | SO$_2$C$_2$H$_4$OH | SO$_2$C$_2$H$_4$OH | H | H | 79.4% | 94.9% |
| 15 | 3-Chloro-2-oxethyl-mercaptobenzaldehyde | H | H | SO$_2$C$_2$H$_4$OH | Cl | 93.1% | 97.5% |
| 16 | 5-Chloro-2-oxethyl-mercaptobenzaldehyde | SO$_2$C$_2$H$_4$OH | H | H | Cl | 94.0% | 96.8% |

EXAMPLE 17

114.8 parts of molten 4-chlorobenzaldehyde are added with stirring within 30 minutes at 35° to 40° C. to a mixture of 213.4 parts of 25% strength potassium hydroxide solution and 88.3 parts of mercaptoethanol. Subsequently, the temperature is raised to 95° C. and the mixture is stirred for 15 hours until reaction is complete (checking by thin-layer chromatography). The mixture is diluted by addition of 50 parts of water. The pH of the reaction mixture is about 9.5 to 10.0.

2 parts of sodium tungstate are now added for the oxidation and 380 parts of 30% strength hydrogen peroxide are added dropwise during the course of 90 minutes, still at 90° to 95° C. The reaction is kept at this temperature for about 18 hours, 200 parts of water are added, and it is cooled to 50° to 60° C. and adjusted to pH 6 using 2N hydrochloric acid.

The mixture is subsequently cooled to 10° to 15° C., the deposited precipitate is filtered off with suction, washed free of salt with ice-water and dried in vacuo at 80° C. 160 parts of 4-oxethylsulfonylbenzoic acid of melting point 168° to 170° C. and a purity of 95.6% (HPLC) are obtained.

If the deposited precipitate is brought into solution at 90° C. after oxidation is complete by the addition of sufficient 2N sodium hydroxide solution (about 400 volume parts), 10 parts of activated charcoal are added to the solution and it is subsequently clarified at 90° C. and the filtrate is then neutralized using 2N hydrochloric acid, then 148 parts of 4-oxethylsulfonylbenzoic acid of melting point 189° to 191° C. and a purity of 98.9% (HPLC) are obtained after cooling, filtering off with suction, washing and drying.

EXAMPLES 18 to 21

If the 4-chlorobenzaldehyde in Example 17 is replaced by aliquot parts of the halobenzaldehyde shown in Table 3 below and the reaction is otherwise carried out in the manner indicated, then the oxyethylsulfonylbenzoic acids of the formula (III) (see below) evident from Table 3 are obtained with the yields and purities (HPLC) stated there.

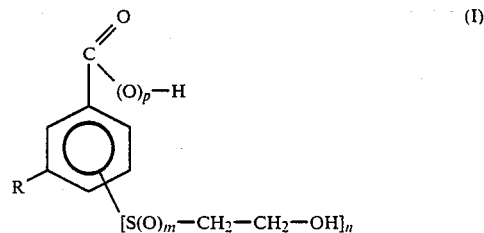

in which R denotes a hydrogen, fluorine, chlorine, bromine or iodine atom, m denotes the number 0, n denotes the number 1 or 2 and p denotes the number 0, and the side-chain —S(O)$_m$—CH$_2$—CH$_2$—OH is in the ortho and para, or ortho or para position to the aldehyde group, which comprises condensing 1 mole of a halobenzaldehyde of the formula (II),

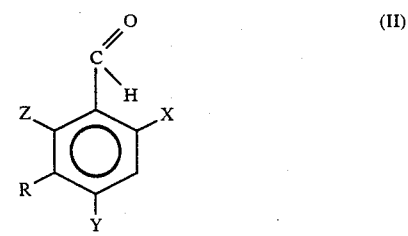

in which R, X, Y and Z represent hydrogen, fluorine, chlorine, bromine or iodine atoms, with the proviso that R, X, Y and Z can be in total 1, 2 or 3 halogen atoms, where R is a halogen atom, if R, X, Y and Z together represent 3 halogen atoms, in aqueous medium with about 1.0 to 15 moles of mercaptoethanol, per halogen atom to be exchanged, in the presence of an acid-binding agent at a temperature of about 70° C. to about 150° C., to give the corresponding oxethylmercaptobenzaldehyde.

TABLE 3

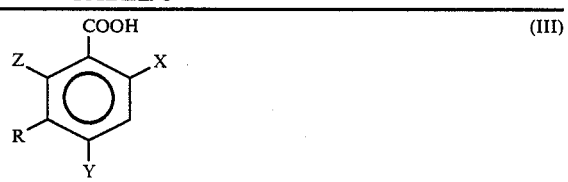

| Ex. | Starting compound | Product X | Y | Z | R | Directly isolated Yield | Purity | Charcoal clarification Yield | Purity |
|---|---|---|---|---|---|---|---|---|---|
| 18 | 3,4-Dichloro-benzaldehyde | H | SO$_2$C$_2$H$_4$OH | H | Cl | 91.8% | 96.8% | 85.3% | 99.1% |
| 19 | 2,5-Dibromo-benzaldehyde | SO$_2$C$_2$H$_4$OH | H | H | Br | 94.1% | 93.4% | 90.5% | 98.5% |
| 20 | 2,3-Dichloro-benzaldehyde | H | H | SO$_2$C$_2$H$_4$OH | Cl | 92.2% | 92.8% | 86.4% | 98.7% |
| 21 | 2-Fluoro-benzaldehyde | SO$_2$C$_2$H$_4$OH | H | H | H | 89.6% | 95.1% | 83.8% | 99.0% |

I claim:

1. A process for the preparation of an oxethylmercaptobenzaldehyde of the formula (1)

2. The process as claimed in claim 1, wherein the condensation is carried out in the presence of caustic soda, sodium hydroxide solution, caustic potash, potassium hydroxide solution or magnesium oxide.

3. The process as claimed in claim 1, wherein the condensation is carried out at temperatures of about 90° C. to about 120° C.

4. The process as claimed in claim 1, wherein 1 mole of the starting compound of the formula (II) mentioned therein is condensed with 1.25 to 1.4 moles of mercaptoethanol.

5. A process for the preparation of an oxethylsulfonylbenzaldehyde of the formula (I)

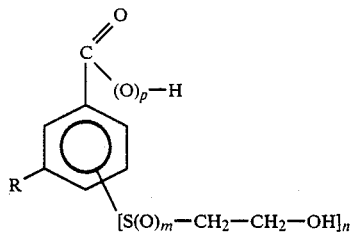

in which R denotes a hydrogen, fluorine, chlorine, bromine or iodine atom, m denotes the number 2, n denotes the number 1 or 2, and p denotes the number 0, and the side-chain $-S(O)_m-CH_2-CH_2-OH$ is in the ortho and para, or ortho or para, position to the aldehyde group, which comprises condensing 1 mole of a halobenzaldehyde of the formula (II)

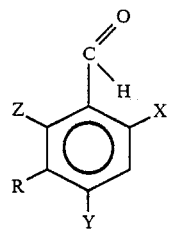

in which R, X, Y and Z represent hydrogen, fluorine, chlorine bromine or iodine atoms with the proviso that R, X, Y and Z can be total 1, 2 or 3 halogen atoms, where R is a halogen atom is R, X, Y and Z together represent 3 halogen atoms, in aqueous medium with about 1.0 to 1.5 moles of mercaptoethanol, per halogen, atoms to be exchanged, in the presence of an acid-binding agent at a temperature of about 70° C. to about 150° C., to give the corresponding oxethylmercaptobenzaldehyde and oxidizing this aldehyde to give the corresponding oxethylsulfonylbenzaldehyde with at least 2 moles of hydrogen peroxide per oxethylmercapto group at a pH<5 at temperature of about 40° C. to about 110° C. in the present of a tungsten (VI) compound as a catalyst.

6. The process as claimed in claim 5, wherein the oxidation is carried out at temperatures of about 60° C. to about 95° C.

7. The process as claimed in claim 5, wherein the oxidation of the oxethylmercaptobenzaldehyde first obtained to give the corresponding oxethylsulfonylbenzaldehyde is performed at a pH between 1 and 4, and wherein said oxidation to give the corresponding oxethylsulfonylbenzoic acid is performed at a pH between 9 and 13.

8. The process as claimed in claim 5, wherein the oxidation is performed in the presence of sodium tungstate or tungsten trioxide as a catalyst.

9. A process for the preparation of an oxethylsulfonylbenzoic acid of the formula

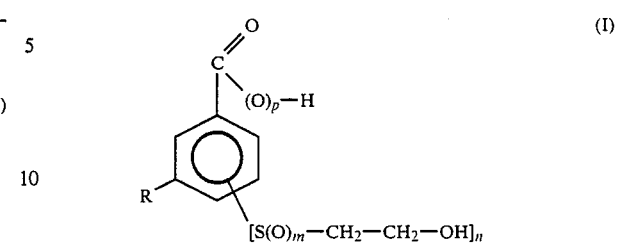

in which R denotes a hydrogen, fluorine, chlorine, bromine or iodine atom, m denotes the number 2, n denotes the number 1 or 2, and p denotes the number 1, and the side-chain $-S(O)_m-CH_2-CH_2-OH$ is in the ortho and para, or ortho or para position to the carboxyl group, which comprises condensing 1 mole of a halogenzaldehyde of the formula (II)

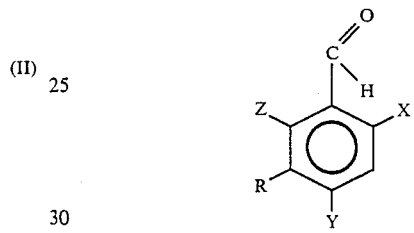

in which R, X, y and Z represent hydrogen, fluorine, chlorine, bromine or iodine atoms, with the proviso that R, X, Y and Z can be total 1, 2 or 3 halogen atoms where R is a halogen atom is R, X, Y and Z together represent 3 halogen atoms, in aqueous medium with about 1.0 to 1.5 moles of mercaptoethanol, per halogen atom to be exchanged, in the presence of an acid-binding agent at temperatures of about 70° C. to about 150° C., to give the corresponding oxethylmercpatobenzaldehyde and oxidizing this aldehyde to give the corresponding oxethylsulfonylbenzoic acid with at least 1 mole of hydrogen peroxide for the oxidation of the aldehyde group and at least 2 moles of hydrogen peroxide per oxethylmercapto group at a pH>8 at temperatures of about 40° C. to about 110° C. in the presence of a tungsten (VI) compound as a catalyst.

10. The process as claimed in claim 9, wherein the oxidation is carried out at temperatures of about 60° C. to about 95° C.

11. The process as claimed in claim 9, wherein the oxidation of the oxethylmercaptobenzaldehyde first obtained to give the corresponding oxethylsulfonylbenzaldehyde is performed at a pH between 1 and 4, and wherein said oxidation to give the corresponding oxethylsulfonylbenzoic acid is performed at a pH between 9 and 13.

12. The process as claimed in claim 9, wherein the oxidation is performed in the presence of sodium tungstate or tungsten trioxide as a catalyst.

* * * * *

UNITED STATES PATENT AND TRADEMARK OFFICE
CERTIFICATE OF CORRECTION

PATENT NO. : 4,922,014
DATED : May 1, 1990
INVENTOR(S) : PAPENFUHS

Page 1 of 3

It is certified that error appears in the above-identified patent and that said Letters Patent is hereby corrected as shown below:

Title page:

In the Abstract, 6 lines from the bottom, -- to -- should be inserted between "70°C" and "about 150°C".

In claim 5, col. 11, line 36,

The ";" after "R" should be a -- , -- .

In claim 5, col. 11, line 37,

"atom is R" should read -- atom if R -- .

In claim 5, col. 11, line 39,

Please delete the "," after "halogen".

In claim 5, col. 11, line 40,

"atoms" should read -- atom -- .

UNITED STATES PATENT AND TRADEMARK OFFICE
CERTIFICATE OF CORRECTION

PATENT NO.  : 4,922,014
DATED       : May 1, 1990
INVENTOR(S) : PAPENFUHS

It is certified that error appears in the above-identified patent and that said Letters Patent is hereby corrected as shown below:

In claim 5, col. 11, line 47,

"present" should read -- presence -- .

In claim 9, col. 12, lines 19-20,

"halogenzaldehyde" should read -- halobenzaldehyde -- .

In claim 9, col. 12, line 32, "y" should read -- Y -- .

In claim 9, col. 12, line 34, please insert "in" between

"be" and "total".

In claim 9, col. 12, line 35, "atom is R" should read

-- atom if R -- .

UNITED STATES PATENT AND TRADEMARK OFFICE
CERTIFICATE OF CORRECTION

PATENT NO. : 4,922,014

DATED : May 1, 1990

INVENTOR(S) : PAPENFUHS

It is certified that error appears in the above-identified patent and that said Letters Patent is hereby corrected as shown below:

In claim 9, col. 12, lines 40-41, "oxethylmercpatobenzaldehyde"
should read -- oxethylmercaptobenzaldehyde --.

Signed and Sealed this

Twentieth Day of August, 1991

*Attest:*

HARRY F. MANBECK, JR.

*Attesting Officer*  *Commissioner of Patents and Trademarks*